United States Patent [19]

Hirose et al.

[11] Patent Number: 5,811,251

[45] Date of Patent: *Sep. 22, 1998

[54] KIT FOR COUNTING THE NUMBER OF LIVING MICROORGANISMS

[75] Inventors: Atsumi Hirose, deceased, late of Kanagawa-ken, by Mari Hirose, legal representative; Susumu Seto, Kanawawa-ken; Takuji Kataoka, Shizuoka-ken, all of Japan; David Wang, Lexington, Mass.

[73] Assignee: Nihon Millipore Kabushiki Kaisha, Tokyo, Japan

[*] Notice: The term of this patent shall not extend beyond the expiration date of Pat. No. 5,627,042.

[21] Appl. No.: 819,424

[22] Filed: Mar. 17, 1997

Related U.S. Application Data

[63] Continuation of Ser. No. 456,350, Jun. 1, 1995, Pat. No. 5,627,042, which is a continuation of Ser. No. 959,232, Oct. 9, 1992, abandoned, which is a continuation of PCT/JP92/00145, Feb. 13, 1992.

[30] Foreign Application Priority Data

Feb. 13, 1997 [JP] Japan ..................................... 3-40615

[51] Int. Cl.$^6$ .............................. C02F 3/00; C12M 1/34; C12N 1/00; G01N 33/53
[52] U.S. Cl. .............................. 435/8; 210/295; 210/615; 435/29; 435/39; 435/243; 435/291; 435/297; 435/300; 435/301; 435/975
[58] Field of Search ..................................... 210/295, 615; 435/8, 29, 39, 243, 291, 297, 300, 301, 975

[56] References Cited

U.S. PATENT DOCUMENTS

| | | | |
|---|---|---|---|
| 3,616,253 | 10/1971 | D'Eustachio et al. ................ | 195/103.5 |
| 3,929,583 | 12/1975 | Sharpe et al. ............................ | 195/127 |
| 4,587,213 | 5/1986 | Malecki ..................................... | 435/39 |
| 4,618,533 | 10/1986 | Steuck .................................. | 428/315.7 |
| 4,908,236 | 3/1990 | Pitt et al. .................................. | 427/245 |
| 5,366,867 | 11/1994 | Kawakami et al. ......................... | 435/8 |
| 5,627,042 | 5/1997 | Hirose et al. ............................... | 435/8 |

FOREIGN PATENT DOCUMENTS

| | | |
|---|---|---|
| 2-57197 | 2/1990 | Japan . |
| 2-163098 | 6/1990 | Japan . |
| 2-57197 | 2/1992 | Japan . |
| 2-163098 | 6/1992 | Japan . |

OTHER PUBLICATIONS

Tsai, T.S., et al., "Rapid Separation and Quantitation of Mixed Microorganisms by Filtration and Bioluminescence (42388)," *Proceedings of the Society for Experimental Biology and Medicine*, 183:74–80 May 1986.

Rodrigues, U.M. and Kroll, R.G., "The direct epifluorescent filter technique (DEFT): increased selectivity, sensitivity and rapidity," *Journal of Applied Bacteriology*, 59:493–500 Jul. 1985.

*Primary Examiner*—David M. Naff
*Assistant Examiner*—Deborah K. Ware
*Attorney, Agent, or Firm*—Hamilton, Brook, Smith & Reynolds, P.C.

[57] ABSTRACT

A rapid, convenient, and highly sensitive method and kit for counting the number of living microorganisms are disclosed. A test solution is filtrated through a membrane filter element having a plurality of hydrophilic sections substantially perfectly separated from each other by hydrophobic partitions. A microparticulate spray is then applied to said filter in order to add extracting and luminescence-inducing reagents in such an amount that allows the filter membrane within each section to become wet. Thereafter the sample obtained is processed by applying a highly sensitive bioluminescence image analyzing system thereto. The employment of a spray method for applying the extracting and luminescence-inducing reagents allows to substantially perfectly entrap the reagents and extracted substances within each of the hydrophilic sections, thus enabling, when combined with the use of a bioluminescence image analyzing system, to rapidly count the number without any or substantial requirement of cultivation.

10 Claims, 1 Drawing Sheet

KIT FOR COUNTING THE NUMBER OF LIVING MICROORGANISMS

This application is a continuation of U.S. patent application Ser. No. 08/456,350, filed on Jun. 1, 1995, now issued as U.S. Pat. No. 5,627,042, which is a continuation of U.S. patent application Ser. No. 07/959,232, filed on Oct. 9, 1992, now abandoned, and a continuation of International Application No. PCT/JP92/01145, filed Feb. 13, 1992. The teachings of the applications are hereby incorporated by reference in their entirety.

FIELD OF THE INVENTION

The present invention relates to a method for counting the number of living microorganisms in a test solution. More paricularly, the invention relates to a rapid, convenient, and highly sensitive method for counting the number of living microorganisms existing in a test solution from, for example, water, raw materials, intermediates, and products used in the industries of foods, pharmacy, cosmetics, electronics, etc.

DESCRIPTION OF THE PRIOR ART

In food, pharmacy, or cosmetic industries, it is well-known that controlling living microorganisms in water, raw materials, intermediates, and final products is of extreme importance. Quality control of industrial water is also a matter of utmost concern in the electronics industry, and one must always be aware of the number of living microorganisms in the water. Consequently, counting the number of living microorganisms is an essential requirement in these industries.

In order to conduct such a measurement, a conventional, so called "standard agar plate method" is generally employed according to the food hygiene testing guidance, in which method living microorganisms in test solutions are cultured on an agar plate medium to form the colonies for their detection. This process, however, is rather troublesome and, moreover, requires a long time for obtaining the results, causing a substantial delay in judgement on the existence of microorganisms or the number thereof. This delay compels one to spare some "waiting time for judgement", particularly during the production or shipment step, thus causing a considerable loss of time and space. Thus, there has been a need in these industries to develop a more rapid and convenient process.

In an attempt to meet this need, a variety of rapid detection methods have been proposed, among which bioluminescence method is known (Japanese Patent No. Tokukai-Hei 2-57,197 and No. Tokukai-Hei 2-163,098; H. Haruta et al.: "Facilitation, Automatization, and Acceleration of Food Microorganism Testing". Science Forum. pp.58. Japan, 1985). The process essentially comprises collecting a small amount of test solution in a small test tube, adding an extracting reagent plus a luminescence-inducing reagent to the solution to determine the amount of adenosine triphosphate (hereinafter referred to as ATP) contained in the microorganisms using a luminometer, and calculating the number of the living microorganisms. The test solution can only be tested directly in the case of the number of microorganisms is sufficiently large, and if it is relatively small, the test solution requires to be filtrated to entrap and concentrate the population of microorganisms in the test solution on a membrane filter, followed by removing the filter, immersing it in a quite small amount of, for example, sterile water to suspend the living microorganisms, and taking a portion of the suspension into a small test tube, before the above mentioned reagents are added.

If the test solution contains an extremely small number of living microorganisms (e.g., from $10^3$ to $10^4$ or less), however, the amount of ATP falls below the lower limit of determination for the luminometer, making this process unfeasible. In such a case, further advanced techniques are required, in which, for example, the membrane filter element with living microorganisms entrapped is placed in a culture medium containing several nutrients suitable for the growth of the microorganisms, and, after the microorganisms are cultured to increase in their number up to the above determination limit, measurement can be carried out. This fact constitutes a major drawback in the method, thus making further improvement inevitable.

On the other hand, there is another method for counting the number of living microorganisms, in which measurement is made after they are filtrated and entrapped within latticed sections of the membrane filter, and cultured to form colonies within the latticed sections, said lattice being made up with a solution of non-wettable hydrocarbon waxes, petroleum jelly, silicone waxes or oils, as well as epoxy, polytetrafluoroethylene or polystyrene resins having been printed on the membrane filter in the shape of square, rectangle, or ring (U.S. Pat. No. 3,929,583).

In this method, as compared with standard agar plate method, microorganisms are prevented from overlapping and adhering mutually, to provide an easier way to measure a dense population of microorganisms, and at the same time high optical contrast between the microbial colonies and the surface of the membrane filter is produced to facilite an automatic measurement of the colonies.

PROBLEMS TO BE SOLVED BY THE INVENTION

The membrane filter according to the above mentioned U.S. patent has not been developed in an initial attempt to detect a single cell of living microorganisms, but in order to measure the colonies formed by entrapping and culturing living microorganisms on a membrane filter. Such a method is a advantageous in that microorganisms are allowed to form colonies separately within the sections of the non-wetting lattice pattern, so that the mutual overlapping of the colonies is prevented, even if a large number of microorganisms are to be counted, thus enabling an accurate measurement of the colonies. On the other hand, the apparatus for counting the number of microorganisms according to said patent is to count the number of colonies that have been grown, isolated within the lattice pattern, after the culture, for example, at 20° C. for 24 hours on said membrane filter. While the method according to said patent provides a non-wettable lattice on a membrane filter to separate colonies, to maintain their state of relatively high density, uniformity, and optical contrast, and to facilitate an accurate automatic measurement of the number of microorganisms, it is not suitable to prevent any overflow and dispersion of the microorganisms to adjacent sections, as required for detecting a single microbial cell to which the present invention is directed, or to prevent the dilution of microbial ingredients caused by a large area of the individual sections, thus none of such a concept is stated in the patent.

In view of the fact that, in order to solve the above mentioned problems, it is inevitable to construct certain hydrophilic sections and to add a required amount of reagents thereto so as to enable to detect the luminescence emitted from even a single cell of living microorganisms, the present invention aims to provide a membrane filter with sections placed thereon, which will achieve more perfect separation among the sections, prevent the extracted ingredients from dispersing or flowing out, and have small areas. Furthermore, the present invention also aims to provide a rapid, convenient, and highly sensitive method for counting the number of living microorganisms through an improved process of adding the reagents for extraction, luminescence inducing, etc., along with a newly incorporated highly sensitive photometric system.

MEANS TO SOLVE THE PROBLEMS

As a result of intensive studies, we have found the following fact and come to the present invention: the above mentioned problems are solved by preparing partitions, which constitute a hydrophobic lattice produced on a membrane filter and slighly protrude therefrom so as to form hydrophilic sections having as small areas as possible within said hydrophobic lattice; thereby preparing membrane filter elements in which the hydrophilic sections are substantially perfectly separated from each other by said partitions; applying a microparticulate spray to the membrane filter in order to add extracting and luminescence-inducing reagents in such an amount that allows the filter membrane within each section to become wet; and thereafter treating the obtained sample with a highly sensitive bioluminescence image analyzing system.

From the above, the present invention provides a method for counting the number of living microorganisms in a test solution, which comprises: filtering said solution through a membrane filter element having a plurality of small hydrophilic membrane filter sections substantially surrounded by a plurarity of hydrophobic partitions, so that said living microorganisms contained in said solution may be entrapped within said sections;

drying said membrane filter element;

spraying an extracting reagent over said membrane filter element to extract a potentially luminescent ingredient of said living microorganisms entrapped within said sections;

spraying a luminescence-inducing reagent over said element to allow said luminescent ingredient to emit luminescence within said sections;

displaying said emitted luminescence as a bright spot, using a bioluminescence image analyzing system; and counting the number of said bright spots as represents the number of living microorganisms in said test solution.

The membrane filter element according to the present invention is formed by dividing a hydrophilic membrane filter into a plurality of hydrophilic sections surrounded by a plurality of hydrophobic partitions. The hydrophilic membrane filter is a finely made film- or sheet-like product of plastic materials, such as hydrophilic polytetrafluoroethylene, hydrophilic poly(vinylidene difluoride), hydrophilic polysulfone, and hydrophilic polyamide, cellulosic materials, such as acetyl cellulose, nitrocellulose, and mixtures thereof, having almost uniform micropores with a pore size from 0.1 to 1 $\mu$m.

A plurality of said small sections comprising hydrophilic membrane filter portions are surrounded by thin, hydrophobic partitions (hereinafter referred to as "partitions"), preferably slightly protruding from the surface of said membrane filter sections. Preferably, the shape of the section is square or rectangular lattice, or a ring, though a honeycomb-like shape may be employed. In order to filter test solutions efficiently, the shape is preferably such that ensures said sections to have wide filter areas, and makes the required processing as easy as possible to provide the partitions, preferably, slightly protruded from the membrane filter. Also, it is preferable that the partition is processed so that it may penetrate and divide the hydrophilic membrane filter into substantially perfect sections. However, since the present invention enables a required amount of reagents to be distributed uniformly, movement of the extracted ingredients and reagents to adjacent sections can be substantially prevented. Thus, desired results of the measurement can successfully be obtained, even if the partition does not penetrate the hydrophilic membrane filter in full thickness from one surface to the other. The height of the partition is generally from 0.01 to 0.05 mm above the surface of the membrane filter, and preferably from 0.02 to 0.04 mm, and its width is generally from 0.1 to 2 mm, and preferably from 0.2 to 1 mm. The area of each section is less than 2 $mm^2$, and preferably less than 1 $mm^2$.

The materials suitable for constructing the partitions include waxes, epoxy resins, silicone waxes, silicone oils, fluorinated resin waxes, polystyrene resins, etc.

In order to form partitions on a hydrophilic membrane filter to compose the membrane filter element as used according to the present invention, it is preferable to deposit the partition materials on the surface of membrane filter within the range of the above dimensions, using, for example, screen printing, relief printing, while other printing methods, including mimeographic printing, anastatic printing, offset printing, transfer printing, and a variety of techniques, such as stamping, line drawing, or screen printing using photosensitive resins, may be used in combination. When the above techniques are applied in order to substantially penetrate the hydrophilic membrane filter in its thickness direction to form the hydrophobic partitions, any suitable solvents and/or monomers and oligomers possessing proper compatibility may be added. After the above process is completed, hydrophobic resins permeate into the hydrophilic membrane filter, allowing portions thereof to become hydrophobic and form hydrophobic partitions in a lattice arrangement which substantially penetrate the membrane filter from one surface to the other.

Alternatively, the membrane filter elements to be used according to the present invention can be produced using a porous hydrophobic membrane: the surface thereof is coated with a monomer capable of crosslinking to form a hydrophilic polymer when irradiated with UV, and thereafter said surface is irradiated with UV to induce said polymerization or copolymerization, with portions which should become said hydrophobic partitions being shaded, or said surface is irradiated with UV through a shading mask during the formation of hydrophilic polymers or copolymers. The unshaded portion thus becomes substantially hydrophilic. Refer to such a method described in U.S. Pat. No. 4,618,533 which is incorporated herein by reference. Preferably, the porous hydrophobic membrane filter may be a membrane of polymers selected in particular from a group consisting of polytetrafluoroe thylene poly(vinylidene difluoride), polycarbonate, polyethylene and polypropylene.

DETAILED DESCRIPTION OF THE INVENTION

Figure 1A:
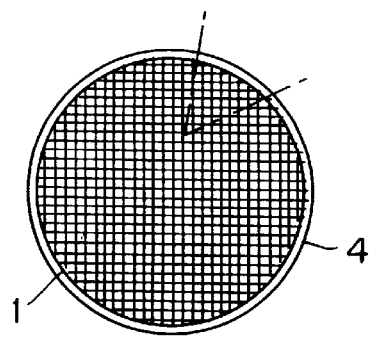
FIG. 1 is a plan view of a membrane filter element according to the present invention, showing its entire appearance 1(A), and an enlarged partial view 1(B) of an area confined by broken lines in 1(A)
Figure 1B:
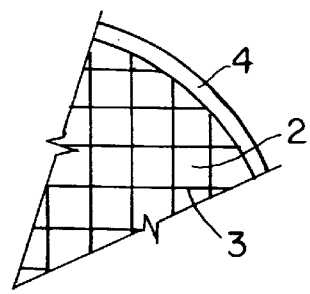

Referring to FIG. 1, the membrane filter element used according to the present invention comprises a sheet of hydrophilic membrane filter 1; portions of said hydrophilic membrane filter 1 consisting of a plurality of small divisions, namely hydrophilic membrane filter sections 2; hydrophobic partitions 3, formed by, for example, printing hydrophobic resins on the membrane filter 1, as described above, to surround said hydrophilic membrane filter sections 2 substantially perfectly not only in planar extent but in vertical extent; and a frame of the membrane filter 1. As previously described, a spray containing extracting and luminescence-inducing reagents is applied to the hydrophilic membrane filter sections 2, immediately after entrapping living organisms. Therefore, it is preferable that the hydrophobic partitions 3 slightly protrude from the surface of said membrane filter sections 2 to prevent the extracted solution, containing the reagents and ATP from the living organisms, from dispersing and flowing out of the particular hydrophilic membrane filter section. Theoretically, this dispersion and overflow can be prevented by applying a spray of particles of smaller size, even if the height of the protrusion is nearly zero. In this case, however, extremely fine microparticles usually require a prolonged time period for completion of spraying, and sometimes fail to achieve a preferable extraction and/or luminescence. It is thus recommended that the hydrophobic partitions 3 protrude up to some height. In addition, a membrane filter element having a large number of smaller area and partitions of narrower width is theoretically preferred, but this will cause an additional restriction of greater difficulties in manufacturing thereof.

In the following, description is made regarding procedures for entrapping extremely small amount of living organisms existing in a test solution, and for counting the number threof.

First, the above mentioned membrane filter element is mounted on a cup-shaped filter container, or the like, such as Hilliflex Filter Unit—Sterifil™ from Nippon Hillipore Limited, etc., so that the test solution is filtered, and living microorganisms are entrapped within a plurality of sections confined with the above mentioned partitions.

Next, the membrane filter is removed and dried, and thereafter an extracting reagent is applied thereto by spraying to extract microbial ingredients on the membrane filter. In carrying out this step, the particle size of spray should be varied according to the area of the membrane filter sections, using, for example, an atomizer, or a nebulizer of either pneumatic or ultrasonic type (hereinafter referred to as "sprayers"). It is preferable that sprayers are those which can effect a uniform and fine spraying, and too close spraying should be avoided. In addition, spraying should be carried out uniformly all over the sections unless an executive amount of reagents should be added to a particular section to disperse the microbial ingredients over the partitions. If the above description is not well attended to, a sufficient accuracy in determination may not be achieved due to dilution of potentially luminescent ingredients.

Subsequently, an luminescence-inducing reagent is sprayed onto the membrane filter sections to induce luminescence. In this step, it is also preferable to carry out the spraying using a sprayer, paying attention to the above descriptions regarding spraying.

The membrane filter element emitting luminescence through the above stated procedures (hereinafter referred to as "sample") is mounted to a sample holder, and, having equipped with a total reflection plate, the sample can be subjected to a bioluminescence image analyzer system (e.g., ARGUS—50/CL™ of tapered fiber input type from Hamamatsu Photonics Co., Ltd. to count the number of living microorganisms. Measurement is carried out by processing the images after accumulation of the luminescence for 2 minutes, further processing the images to eliminate any luminescence which is considered as a noise, and finally counting the number of remained bright spots.

The bioluminesence image analyzing system used herein is a novel and indeed innovative device, in which even such a faint luminescence that could not be detected through conventional instruments can be detected with high sensitivity, and intensified for processing. Also, the processing and analysis of data are carried out rapidly and conveniently. Moreover, said system enables to detect even a single living microbial cell, in cooperation with the effect of spraying using an unusual membrane filter and a reagent sprayer according to the present invention, thereby considerably contributing to the realization of this unusually excellent counting method.

Figure 3A:
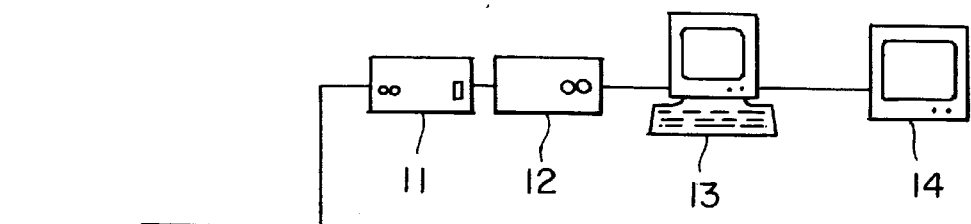
FIG. 3 is a schematic diagram of a bioluminescence image analyzing system used according to the present invention, showing its entire composition 3(A), and an enlarged partial view 3(B) of an area confined by a circle in 3(A).
Figure 3A:
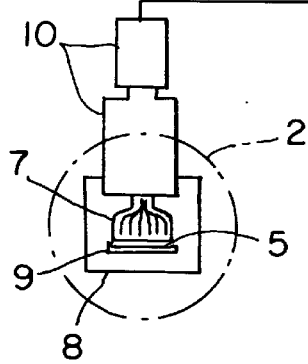
Figure 3B:
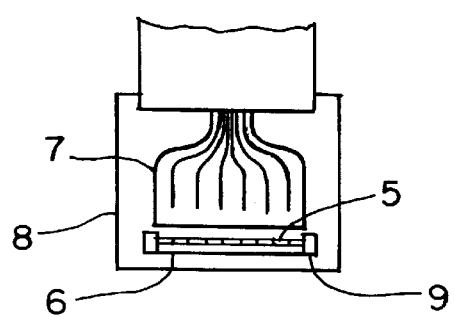

The outline of the system is shown in FIG. 3. This system comprises a sample holder 9 for supporting a membrane filter element (sample) 5 after treatment with the above mentioned extracting and luminescence-inducing reagents: a total reflection plate 6; shading housing 8; a tapered fiber 7, juxtaposed to said membrane filter element as closely as possible to detect luminescence in a two-dimensional extent; an ultrahighly sensitive television camera 10 consisting of a photoamplifying component and a camera tube; a camera controller 11; an image processor 12; a data analyzing apparatus 13; and a monitor television 14. The system equipped with ARGUS—50/CL™ of tapered fiber input type from Hamamatsu Photonics Co., Ltd., or those having a similar counting performance is particularly preferred. As an ultrahighly sensitive television camera, those enabling to restrain the noises from the camera itself to accumulate even a very faint luminescence, by cooling to the temperature from about −30° to −12° C. using a cooled solid state camera device (CCD) may be employed. For example, a cooled CCD digital imaging system from Hamamatsu Photonics is available. Alternatively, the above procedure can be carried out by inverting both the tapered fiber 7 in the camera tube portion and the ultrahighly sensitive television camera 10, and placing thereon a sample holder containing a sample.

Sample 5 is preferably placed as closely as possible to tapered fiber 7 therby to significantly enhance the measurement sensitivity. On demand, sprayer(s) for extracting and luminescence-inducing reagents and sample carrier, etc. may be set in combination in order to carry out an automatic counting.

To count the number of living microorganisms, sample holder 9, bearing the sample (membrane filter element retaining microorganisms to be examined) after luminescence-inducing treatment, is placed in close contact with surfaces of the tapered fibers 7, then, the luminescence emitted from microbial bodies is introduced through ultrahighly sensitive television camera 10 and camera controller 11 into image processor 12, where photons are accumulated for 30 through 180 seconds, e.g., 120 seconds in a two-dimensional extent to pick up the image. Data analyzing apparatus 13 then processes the image to eliminate any weaker noise luminescence, and displays, at monitor television 13, the only remained bright luminescence originated from living microorganisms as a bright spot. By this processing, luminescence from other than microbial bodies are erased, resulting in substantial correspondence of the counted number of bright spots to the number of living microorganisms.

In the most preferred embodiment of the present invention, the microbial ingredient to be extracted is ATP. In this case, ATP extracting reagent (e.g., NRB™, Lumac Co.) is used as an extracting reagent, and the reagent is sprayed in the form of very fine particles, using a sprayer (e.g., Ultrasonic Aspirator™, Matsushita Electric Industries Co., Ltd.), to extract ATP from living organisms entrapped within the membrane filter sections. Luminescence-inducing reagent (e.g., Lumit-PM™, Lumac Co.) is also sprayed in a similar manner, to induce luminescence. As stated above, thus obtained sample is then subjected to the above bioluminescence image analyzing system to accumulate the luminescence for 30 through 180 seconds, and to display the only luminescence brighter than backgroud luminescence as a bright spot in the monitor television. To determine the maximum brightness of the background luminescence (i.e., background level), an equal volume of the same test solution as is to be examined is prepared and sterilized. After filtering this solution on the membrane filter according to the present invention, the membrane filter is treated in the same manner as described above to induce luminescence. The maximum brightness of the bright spot displayed in the monitor television when thus obtained sample is subjected to said bioluminescence image analyzing system is the background level (hereinafter referred to as "threshold"). Accordingly, when luminescence that emits less bright light than the threshold is completely eliminated, the bright spots displayed in the monitor television from the rest of the luminescence (i.e., luminescence brighter than the threshold) directly represent the luminescence originated from living microorganisms.

EFFECTS OF THE INVENTION

In the present invention, a membrane filter element consisting of a plurarity of small membrane filter sections and having hydrophobic partitions slightly protruding above the filter surface is employed, so that all the living microorganisms are entrapped within any one of said sections. Subsequently, an extracting solution (ATP extracting solution) and luminescence-inducing reagent (luciferin-liciferase reagent) are sprayed in a particulate state, so that the reagents remain within the particular membrane filter sections, neither dispersing out of the sections nor undergoing any dilution. In addition, such a contrivance is made that the dilution within a section may be retarded so far as possible. Luminescent microbial ingredients are thereby retained in higher concentrations, which enables to easily determine even an extremely small amount of microbial ingredients.

Moreover, by subjecting samples (membrance filter element) thus allowed to emit luminescence to a bioluminescence image analyzing system, it has become possible to detect a faint luminescence from a single subject in two-dimensional extent, enabling to count the number of living microorganism automatically, highly sensitively, rapidly, and conveniently, even when the number is extremely small. In other words, employment of a television camera head composed of a tapered fiber, photoamplifier, and a camera tube has enabled luminescence originated from living microorganisms to be indicated (recognized) as very bright spots, so that any noise luminescence from other materials than living microorganisms can easily be eliminated in comparison with a threshold luminescence, thus enabling to count the number of living microorganisms automatically, rapidly, and conveniently, even when the number is extremely small (e.g., less than a few cells/100 ml of test solution). In addition, there may be a case wherein it is rather significant to judge the existence of a single living microorganism in sample solutions, as of the case in coliform test for foods or cooling beverages. While the present invention is nearly always applicable, the membrane filter element after filtering test solutions and entrapping living microorganisms are, more preferably, placed on a pad or nutrient agar plate containing the most suitable nutrients for the growth of said living microorganisms. When subjected to the counting after the living microorganisms have grown within the same sections by a short-term (e.g., several hours) culture, significantly luminous bright spots will be available, thus providing a more accurate judgement means. The culturing condition to such extent does not naturally allow a single cell to form any colonies.

EXAMPLES

The present invention will be further illustrated by the following examples.

Example 1

*Saccharomyces cerevisiae* (IFO 0209) cultured in a glucose peptone medium (Eiken Chemicals Co., Ltd.) at 30° C. for overnight was diluted with physiological saline to microbial concentration of about 20 CFU/ml (CFU: colony forming unit), and 1 ml of the solution was collected as a test solution.

Figure 2:
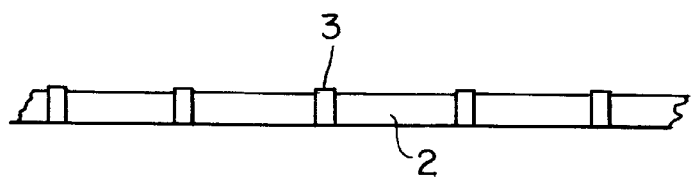
FIG. 2 is a sectional enlarged partial view of said membrane filter element.

On a membrane filter made of hydrophilic polycabonate with pore size of 0.45 μm and diameter of 25 mm, latticed hydrophobic partitions as shown in FIGS. 1 and 2 were printed, using an ink of well transmittable and readily curable properties with UV irradiation, and conventional screen printing technique, to obtain a membrane filter element comprising square-shaped hydrophilic sections with side length of 0.5 mm surrounded by the partitions with height above the surface of the memebrane of 20 μm and width of 0.2 mm.

Using a filter equipment fitted with this membrane filter element, the above test solution was sucked and filtered.

The membrane filter was then removed from the filter equipment, dried, and mounted on a sample holder. An ATP extracting reagent made by Lumac Co. (NRB™) was sprayed onto the membrane filter for 10 seconds using an atomizer (Koike Chemicals Co.) held above it in an angle of 45° at a distance of about 15 cm, carefully lest large droplets should be splashed. After 20 seconds, luciferin-luciferase luminescence-inducing reagent Lumit-PM™, Lumac Co.) was sprayed for 10 seconds using the same atomizer, to allow the membrane filter to emit luminescence. Then, the membrane filter was subjected to ARGUS—50/CL™ bioluminescence image analyzing system (Hamamatsu Photonics Co.), and photon accumulation was carried out for 2 minutes. After displaying the luminescence as bright spots on the television monitor, noise luminescence was eliminated to count the number of living microorganisms. The results obtained are shown in Table 1.

As the comparison experiment, the similar test solution as above was subjected to counting the number of living microorganisms after culturing at 30° C. for 48 hours using standard agar plate method. The results are also shown in Table 1.

TABLE 1

| Exp. No. | Standard Agar Plate (CFU/ml test solution) | Present Invention (bright spot/element) |
| --- | --- | --- |
| 1 | 15 | 12 |
| 2 | 21 | 19 |
| 3 | 19 | 20 |

Example 2

*Saccharomyces cervisiae* (IFO 0209) cultured in the same manner as described in Example 1 was diluted with physiological saline to microbial concentration of about 200 CFU/ml, and 1 ml of the solution was collected as a test solution. Following the same procedures as described in Example 1 to count the number of the bright spots, the results shown in Table 2 were obtained.

TABLE 2

| Exp. No. | Standard Agar Plate (CFU/ml test solution) | Present Invention (bright spot/element) |
| --- | --- | --- |
| 1 | 230 | 210 |
| 2 | 250 | 261 |
| 3 | 215 | 202 |

Example 3

*Pseudomonas diminuta* (IFO 14213) was diluted with physiological saline to microbial concentration of about 50 CFU/ml, and 1 ml was collected as a test solution.

On a membrane filter made of hydrophilic polytetrafluoroethylene with pore size of 0.45 µm and diameter of 25 mm, square-shaped hydrophilic sections with side length of 0.4 mm, and partitions with height of 20 µm and width of 0.3 mm were produced using an ink permeating into the membrane to some degree, of well transmittable and readily curable properties by UV irradiation, and the conventional screen printing technique. Using thus obtained membrane filter element, the test solution was filtered as described in Example 1. The membrane filter was then removed, dried, extracted, and allowed to emit luminescence as described in Example 1. After it was subjected to image analyzing process to eliminate background luminescence, the number of bright spots were counted. The results are shown in Table 3, along with those obtained by counting the number of living microorganisms using the standard agar plate method for the similar test solutions.

TABLE 3

| Exp. No. | Standard Agar Plate (CFU/ml test solution) | Present Invention (bright spot/element) |
| --- | --- | --- |
| 1 | 62 | 53 |
| 2 | 45 | 41 |
| 3 | 48 | 46 |

Example 4

*Escherichia coli* (IFO 13898) was diluted with physiological saline to microbial concentration of about 100 CFU/ml, and 1 ml of the solution was collected as a test solution. Using the membrane filter element prepared in the same way as Example 3, and following the same procedures as described in Example 1, the test solution was filtered. Then, the membrane filter was removed, dried, extracted, and allowed to emit luminescence. After it was subjected to image analyzing process to put out background luminescence, the number of bright spots was counted. The results are shown in Table 4, along with those obtained by using the standard agar plate method for the similar test solutions.

TABLE 4

| Exp. No. | Standard Agar Plate (CFU/ml test solution) | Present Invention (bright spot/element) |
| --- | --- | --- |
| 1 | 113 | 108 |
| 2 | 105 | 112 |
| 3 | 106 | 98 |

Example 5

To a test tube containing 5 ml of glucose peptone medium (Eiken Chemicals Co., Ltd.), a platinum loop of *Saccharomyces cerevisiae* (IFO 0209) was inoculated, and cultured at 30° C. for overnight. After the medium was diluted with phosphate buffer solution (pH=7.2) to microbial concentration of about 10 CFU/ml, 1 ml of the solution was collected as a test solution.

A membrane filter element was used, in which latticed hydrophobic partitions with height of 20 µm and width of 0.3 mm were printed on a membrane filter (25 mm diameter) made of hydrophilic poly(vinylidene difluoride), using an ink permeating into the membrane to some degree, of well transmittable and readily curable properties by UV irradiation, and the conventional screen printing technique, to form square-shaped hydrophilic membrane filter sections with side length of 0.3 mm. After filtrating 1 ml of the test solution, the membrane filter was washed, and dried, then an extracting reagent (NRB™, Lumac CO.) was sprayed for 10 seconds through an ultrasonic type sprayer (Matsushita Electric Industries) at a distance of about 10 cm, followed by spraying a luminescence-inducing reagent (Lumit-PM™, Lumac Co.) for 10 seconds in the same way as above. The membrane filter was then subjected to image analyzing process in the same procedures as in Example 1, using a system as described referring to FIG. 3, to eliminate any noise luminescence. The number of bright spots was counted to obtain results as shown in Table 5.

TABLE 5

| Exp. No. | Standard Agar Plate (CFU/ml test solution) | Present Invention (bright spot/element) |
| --- | --- | --- |
| 1 | 12 | 10 |
| 2 | 9 | 8 |
| 3 | 13 | 10 |

Example 6

To a test tube containing 5 ml of m-TCE medium (DIFCO LABORATORIES), a platinum loop of *Escherichia coli* (IFO 13898) was inoculated, and cultured at 37° C. for overnight. After the medium was diluted with phosphate buffer solution (pH=7.2) to microbial concentration of about 10 CFU/ml, 1 ml of the solution was collected as a test solution.

Using a similar membrane filter element as described in Example 5. 1 ml of the test solution was filtered. After the membrane filter was washed, and dried, extracting and luminescence inducing processes were carried out, to subject to image analyzing process. Noise luminescence were put out, and the number of bright spots was counted. On the other hand, another membrane filter element after filtering 1 ml of the above test solution was placed on a pad soaked with m-TGE medium, cultured at 37° C. for 4 hours, then subjected to extracting and luminescence-inducing processes. After further processes for image analysis and noise elimination, the number of bright spots was counted. These results are shown in Table 6.

TABLE 6

| Exp. No. | Standard Agar Plate CFU/ml test solution | Direct Meas. bs/e* | Direct Meas. bi** | Meas. After Culture bs/e* | Meas. After Culture bi* |
|---|---|---|---|---|---|
| 1 | 11 | 9 | 24 | 9 | 114 |
| 2 | 9 | 7 | 22 | 8 | 163 |
| 3 | 13 | 9 | 19 | 11 | 128 |

*bright spots/membrane filter element.
**light intensity of bright spots. indicating the maximum brightness of bright spots originated from living microorganisms obtained on the television monitor.

Example 7

To a test tube containing 5 ml of m-TGE medium (DIFCO LABORATORIES), a platinum loop of *Streptococcus faecalis* (IFO 12580) was inoculated, and cultured at 37° C. for overnight. After the medium was diluted with phosphate buffer solution (pH=7.2) to microbial concentration of about 30 CFU/ml, 1 ml of the solution was used as a test solution. Using a similar membrane filter element, and following the same procedures as described in Example 5, the membrane filter element was cultured for 4 hours, dried, extracted, and allowed to emit luminescence. After carrying out the image analysis and noise elimination, the number of bright spots was counted to obtain the results as shown in Table 7.

TABLE 7

| Exp. No. | Standard Agar Plate (CFU/ml test solution) | Present Invention (bright spot/element) |
|---|---|---|
| 1 | 39 | 31 |
| 2 | 30 | 28 |
| 3 | 35 | 30 |

Example 8

100 ml of commercially obtained canned beer (Asahi Breweries Co.) was filtrated axenically. To the filtered, 2 ml of a solution containing about 30 CFU/ml of *Saccharomyces cervisiae* (IFO 0209) cultured in the same way as described in Example 5 and diluted with phosphate buffer solution (pH=7.2) was added to prepare a test solution.

A membrane filter made of hydrophobic polytetrafluoroethylene with pore size of 0.45 $\mu$m, diameter of 25 mm, and thickness of 50 $\mu$m was wetted down with methanol, and washed with water following the procedure described in Example 34 in U.S. Pat. No. 4.618,533 (to Michael J. Steuck). It was then immersed in an aqueous solution containing 5% of hydroxypropyl acrylate. 1% of glycidyl acrylate, and 1% of ammonium persulfate, and interposed between two sheets of polyethylene film both consisting of square-shaped transmitting portions with side length of 0.5 mm and latticed shading portions with width of 0.2 mm surrounding the transmitting portions, with both sheets being aligned with each other regarding the shading portions. After UV irradiation, the membrane filter was washed with water, then with methanol, and was dried. During the above process the membrane filter becomes hydrophilic in the transmitting portions.

Using thus obtained membrane filter element, and following the same procedures as described in Example 5, the test solution was filtered, and the membrane filter element was washed, dried, extracted, and allowed to emit luminescence. Then, image analyzing process was carried out using the system as descibed referring to FIG. 3, to put out any noise luminescence, and the number of bright spots was counted to obtain the results as shown in Table 8.

TABLE 8

| Exp. No. | Standard Agar Plate (CFU/ml test solution) | Present Invention (bright spot/element) |
|---|---|---|
| 1 | 63 | 61 |
| 2 | 60 | 56 |
| 3 | 67 | 64 |

Example 9

100 ml of commercially obtained canned coca-cola (Nippon COCA-COLA® soda Bottlers Inc.) was filtered axenically. To the filtrate, 3 ml of a solution containing about 10 CFU/ml of *Saccharomyces cervisiae* (IFO 0209) cultured in the same way as descibed in Example 5 and diluted with phosphate buffer solution (pH=7.2) was added to prepare a test solution.

Using a similar membrane filter as described in Example 8, and following the same procedures as described in Example 5, the test solution was filtered, and the membrane filter element was washed, dried, extracted, and allowed to emit luminescence. Then, image analyzing process was carried out to put out any noise luminescence, and the number of bright spots was counted to obtain the results as shown in Table 9.

TABLE 9

| Exp. No. | Standard Agar Plate (CFU/ml test solution) | Present Invention (bright spot/element) |
|---|---|---|
| 1 | 31 | 29 |
| 2 | 33 | 27 |
| 3 | 30 | 27 |

We claim:

1. A kit for counting the number of living microorganisms in a test solution comprising:
    (a) a membrane filter element having a plurality of hydrophilic membrane filter sections surrounded by a plurality of hydrophobic partitions;
    (b) an ATP-extracting reagent; and
    (c) a luminescence-inducing reagent.

2. The kit according to claim 1 wherein the luminescence-inducing reagent is in a spray bottle.

3. The kit according to claim 1 wherein the ATP-extracting reagent is in a spray bottle.

4. The kit according to claim 1, further comprising a culture medium for growth of said living microorganisms.

5. The kit according to claim 1, wherein said hydrophobic partitions protrude from the surface of said hydrophilic membrane filter sections.

6. The kit according to claim 5, wherein said hydrophobic partitions protrude by the height from 0.01 to 0.05 mm above said surface of the hydrophilic membrane filter sections, and have a width from 0.1 to 2 mm.

7. The kit according to claim 1, wherein said luminescence-inducing reagent is luciferin-luciferase reagent.

8. The kit according to claim 1, wherein each of said hydrophilic membrane filter sections has the surface area between 0.04 mm$^2$ and 2 mm$^2$.

9. The kit according to claim 1, wherein said membrane filter element having a plurality of hydrophilic membrane filter sections substantially surrounded by hydrophobic partitions is a composite membrane obtained by coating the surface of a porous hydrophobic membrane filter with a monomer capable of crosslinking to form a hydrophilic polymer when irradiated with ultraviolet light and thereafter irradiating said surface with ultraviolet light to induce a polymerization or copolymerization in said hydrophobic membrane filter, with portions shaded from ultraviolet light becoming said hydrophobic partitions.

10. The kit according to claim 9, wherein said porous hydrophobic membrane filter is made of material selected from the group consisting of polytetrafluoroethylene, poly (vinylidene difluoride), polyethylene, polypropylene and polycarbonate.

\* \* \* \* \*